US009974816B2

(12) United States Patent
Garssen et al.

(10) Patent No.: US 9,974,816 B2
(45) Date of Patent: May 22, 2018

(54) SYNBIOTICS COMBINATION FOR BRAIN IMPROVEMENT

(71) Applicant: N.V. Nutricia, Zoetermeer (NL)

(72) Inventors: Johan Garssen, Utrecht (NL); Ruurd Van Elburg, Utrecht (NL); Nana Bartke, Utrecht (NL); Aletta Desiree Kraneveld, Nigtevecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days. days.

(21) Appl. No.: 14/440,299

(22) PCT Filed: Nov. 4, 2013

(86) PCT No.: PCT/NL2013/050785
§ 371 (c)(1),
(2) Date: May 1, 2015

(87) PCT Pub. No.: WO2014/070016
PCT Pub. Date: May 8, 2014

(65) Prior Publication Data
US 2015/0366919 A1 Dec. 24, 2015

Related U.S. Application Data

(60) Provisional application No. 61/721,833, filed on Nov. 2, 2012.

(30) Foreign Application Priority Data

Nov. 2, 2012 (EP) .................................... 12191171

(51) Int. Cl.
A61K 35/745 (2015.01)
A61K 31/198 (2006.01)
A61K 31/702 (2006.01)
A61K 45/06 (2006.01)
A61K 31/202 (2006.01)
A61K 31/715 (2006.01)
A61K 31/733 (2006.01)
A61K 9/00 (2006.01)
A23L 33/00 (2016.01)
A23L 33/12 (2016.01)
A23L 33/135 (2016.01)
A23L 33/175 (2016.01)
A23L 33/18 (2016.01)
(Continued)

(52) U.S. Cl.
CPC ............ A61K 35/745 (2013.01); A23L 33/12 (2016.08); A23L 33/135 (2016.08); A23L 33/175 (2016.08); A23L 33/18 (2016.08); A23L 33/21 (2016.08); A23L 33/40 (2016.08); A61K 9/009 (2013.01); A61K 31/198 (2013.01); A61K 31/202 (2013.01); A61K 31/702 (2013.01); A61K 31/715 (2013.01); A61K 31/733 (2013.01); A61K 45/06 (2013.01); A23V 2002/00 (2013.01); A23V 2200/00 (2013.01); A23Y 2300/29 (2013.01); A61K 2035/115 (2013.01)

(58) Field of Classification Search
CPC ...... C12R 1/07; A61K 35/745; A61K 31/198; A61K 31/702
See application file for complete search history.

(56) References Cited

U.S. PATENT DOCUMENTS

2003/0138476 A1 7/2003 Van Leeuwen et al.
2007/0207132 A1 9/2007 Speelmans et al.
(Continued)

FOREIGN PATENT DOCUMENTS

EP 2 308 498 A1 4/2011
EP 2 335 502 A1 6/2011
(Continued)

OTHER PUBLICATIONS

Adesanya Olubukunola, A. et al., "Intestinal perforation in very low birth weight infants: growth and neurodevelopment at 1 year of age", Journal of Perinatology: Official Journal of the California Perinatal Association, vol. 25, No. 9, Sep. 2005, pp. 583-589.
De Kieviet Jorrit, F. et al., "Effects of glutamine on brain development in very preterm children at school age", Pediatrics, American Academy of Pediatrics, Evanston, IL, US, vol. 130, No. 5, Nov. 1, 2012, pp. e1121-e1127.
De Kieviet Jorrit, F. et al., "Effects of neonatal enteral glutamine supplementation on cognitive, motor and behavioural outcomes in very preterm and/or very low birth weight children at schools age", British Journal of Nutrition, Cambridge Univ. Press, UK, vol. 108, No. 12, Dec. 1, 2012, pp. 2215-2220.
(Continued)

Primary Examiner — Ruth A Davis
(74) Attorney, Agent, or Firm — Gilberto M. Villacorta; Sunit Talapatra; Foley & Lardner LLP

(57) ABSTRACT

The invention relates to nutritional compositions with Bifidobacterium breve and non-digestible oligosaccharides selected from the group consisting of fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides for use in improving cognitive or behavioral performance, cognitive or behavioral development, social interaction and/or neuroinflammation in infants or toddlers. Also claimed is the use of a nutritional compositions including Bifidobacterium breve, at least one non digestible oligosaccharide, glutamine in the form of free amino acids and/or glutamine containing dipeptide and/or glutaime containing tripeptide and LC-PUFA in the form or arachidonic acid and/or docosahexaenoic acid. Also claimed is a kit of parts comprising a first container comprising glutamine, and a non-digestible oligosaccharide and a second container comprising Bifidobacterium breve.

14 Claims, No Drawings

(51) Int. Cl.
*A23L 33/21* (2016.01)
*A61K 35/00* (2006.01)

(56) References Cited

U.S. PATENT DOCUMENTS

| | | |
|---|---|---|
| 2008/0241226 A1 | 10/2008 | Abeln et al. |
| 2009/0162323 A1* | 6/2009 | Boehm ................ A23C 9/1234 424/93.4 |
| 2010/0278781 A1 | 11/2010 | Hougee et al. |
| 2011/0086809 A1 | 4/2011 | Anthony et al. |
| 2011/0208153 A1 | 8/2011 | Alvey |
| 2012/0171165 A1 | 7/2012 | Buck et al. |
| 2013/0095204 A1* | 4/2013 | Jouni ...................... A23L 33/19 426/2 |

FOREIGN PATENT DOCUMENTS

| | | | |
|---|---|---|---|
| WO | WO 2008/015374 | * | 2/2008 |
| WO | WO-2008/108651 A1 | | 9/2008 |
| WO | WO-2008/111832 A1 | | 9/2008 |
| WO | WO-2011/017107 A1 | | 4/2011 |
| WO | WO-2011/051482 | | 5/2011 |
| WO | WO-2012/092160 | | 7/2012 |
| WO | WO-2013/105851 A1 | | 7/2013 |

OTHER PUBLICATIONS

Field et al., "A comparison of symptoms used by mothers and nurses to identify an infant with colic", International Journal of Nursing Studies, Pergamon, Amsterdam, NL, vol. 3I, No. 2, Apr. 1, 1994, pp. 201-215.

International Search Report of PCT/NL2013/050785 dated May 8, 2014.

Kin, B. et al., "Learning ability-improving compsn.—contains sialic acid-contg. oligo:saccharide", WPI/Thomson, vol. 1996, No. 51, Oct. 15, 1996.

* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: GAPDH F-primer

<400> SEQUENCE: 1
gcatcctgca ccaccaactg                                              20

<210> SEQ ID NO 2
<211> LENGTH: 20
<212> TYPE: DNA
<213> ORGANISM: Artificial
<220> FEATURE:
<223> OTHER INFORMATION: GAPDH R-primer

<400> SEQUENCE: 2
acgccacagc tttccagagg                                              20

<210> SEQ ID NO 3
<211> LENGTH: 21
<212> TYPE: DNA
<213> ORGANISM: Artificial
<220> FEATURE:
<223> OTHER INFORMATION: BDNF F-primer

<400> SEQUENCE: 3
```

```
gaaggctgca ggggcataga c                                              21
```

<210> SEQ ID NO 4
<211> LENGTH: 24
<212> TYPE: DNA
<213> ORGANISM: Artificial
<220> FEATURE:
<223> OTHER INFORMATION: BDNF R-primer

<400> SEQUENCE: 4

```
tacacaggaa gtgtctatcc ttat                                           24
```

SYNBIOTICS COMBINATION FOR BRAIN IMPROVEMENT

CROSS-REFERENCE TO RELATED APPLICATIONS

This application is the National Phase of International Patent Application No. PCT/NL2013/050785, filed Nov. 4, 2013, published as WO 2014/070016, which claims priority to European Application No. 12191171.3 and U.S. Provisional Application No. 61/721,833, both filed Nov. 2, 2012. The contents of these applications are herein incorporated by reference in their entirety.

The instant application contains a Sequence Listing which has been submitted in ASCII format via EFS-WEB and is hereby incorporated by reference in its entirety. Said ASCII copy, created on Sep. 9, 2015, is named sequence.txt and is 1 KB.

FIELD OF THE INVENTION

The present invention relates to nutritional compositions comprising synbiotics for use in improving brain and cognitive performance, particularly social interaction and spatial memory performance. The invention is in particular suitable for infants with an age of 6 month or below, preterm infants, and for infants or young children suffering from inflammation, allergy or atopic disease.

BACKGROUND OF THE INVENTION

Increasing attention is raised towards the connection between the gut and the brain and the role nutrition plays in this connection. A complex, bidirectional communication system exists between the gut and the brain, which ensures gastrointestinal homeostasis and digestion maintenance, and which in reverse direction may affect cognitive and psychological function and behavior. In some subjects this connection between the gut and brain is disturbed resulting in a co-morbidity between intestinal inflammation and increased anxiety, depression, altered pain sensitivity and/or decreased cognitive performance.

Especially in infants and toddlers such co-morbidity is unwanted since during infancy the cognitive system is still developing, and the disturbance of this development may have long lasting effects. Peri-natal brain plasticity increases the vulnerability to early stress conditions, such as repetitive pain, or inflammation, which may lead to abnormal cognitive development and behavior.

Breast-feeding is the preferred method of feeding infants. However, there are circumstances that make breast-feeding impossible or less desirable. In those cases infant formulae are a good alternative. The composition of modern infant formulae is adapted in such a way that it meets many of the special nutritional requirements of the fast growing and developing infant. Still further improvements can be made. The present invention relates to nutritional compositions for infants, in particular infant formulae, which comprises specific ingredients for improving cognitive performance and behaviour.

WO 2012/092160 and US2012/0171165 disclose nutritional compositions including human milk oligosaccharides that can be administered to individuals including preterm infants, infants, toddlers and children for improving gastrointestinal function and tolerance, as well as the growth of beneficial bacteria. Additional suitable methods of using the nutritional compositions including human milk oligosaccharides are also disclosed. WO 2011/051482 discloses nutritional compositions for infants and/or children comprising lactoferrin and probiotics. WO 2008/111832 discloses a therapy aimed at language and/or social skills in infants through administration of components stimulating the development of a healthy intestinal flora.

WO 20011/047107 and US 2011/086809 disclose a method for supporting retinal, intestinal and/or nervous system development in a neonate, providing arginine-glutamine dipeptide. Many, many further ingredients are listed as part of infant formulae which may be used to administer the dipeptide. The effects supported in the examples are the prevention of retinopathy of prematurity in a mouse model of oxygen-induced retinopathy, and the protection against intestinal and brain injury induced by hyperoxia in a mouse model monitoring caspase-3 activity and 'intestinal damage score'.

US 2007/207132 discloses a preparation comprising *Bifidobacterium breve* and a mixture of non-digestible carbohydrates for non- or partially breast-fed infants as well as the use thereof for the treatment of prevention of immune disorders in non- or partially breast-fed infants.

According to the abstract, JP19950099779 discloses a learning-ability improving composition containing a sialic acid-containing oligosaccharide derivative.

Olubukunola et al. "*Intestinal perforation in very low birth weight infants: growth and neurodevelopment at 1 year of age*" J. Perinatology vol. 25, no. 9 (2005) 583-589 [XP002704986] compares growth and neurodevelopment in surviving very low birth weight infants with an intestinal perforation caused by necrotizing enterocolitis versus spontaneous intestinal perforation. No intervention was disclosed.

Field et al. "*A comparison of symptoms used by mothers and nurses to identify an infant with colic*" Int. J. Nursing Studies vol. 31, no. 2 (1994) 201-215 [XP022870583] addresses ways in which parents believe to identify colic with a variety of factors, including eating behavior, maternal anxiety, baby's and mother's diets, and baby's stress. No intervention was disclosed.

US 2011/208153 describes formulations and methods for delivering water-soluble and lipid-soluble nutrients for preventing or correcting nutrient deficiencies to subjects requiring small-volume nutritional support, such as preterms. The nutritional formulation comprising fatty acids such as DHA and/or ARA, amino acids such as arginine and glutamine and other nutrients is suitable for delivery via nasogastric tube, intragastric feeding and transpyloric administration. Among many other components, prebiotics are merely mentioned as a further ingredient. *B. breve* is not mentioned among the various ingredients, and, according to its background description, glutamine may be an ingredient as a primary fuel for rapidly dividing cells, such as intestinal enterocytes and lymphocytes.

De Kieviet et al. "*Effects of glutamine of brain development in very preterm children at school age*" Pediatrics vol. 130, no. 5 (2012) 1121-1127 [SP009168039] studies the effect of short-term administration of glutamine to very preterm children in the first month after birth on brain development later in life, at school age. A similar study is reported in, De Kieviet et al. "*Effects of neonatal enteral glutamine supplementation on cognitive, motor and behavioral outcomes in very preterm and/or very low birth weight children at school age*" British J. Nutrition vol 108, no. 12 (2012) 2215-2220. Based on the behavioral outcome tests used there, it was concluded that glutamine supplementation between day 3 and day 30 of life had neither beneficial nor detrimental effects on long-term cognitive, motor and behavioral outcomes of very preterm and/or VLBW children at school age, although visuomotor abilities were poorer in children that received glutamine.

SUMMARY OF THE INVENTION

The inventors surprisingly found when employing animal models that dietary supplementation with *Bifidobacterium breve* in combination with non-digestible oligosaccharides, preferably further in combination with glutamine, resulted in improved cognitive and behavioral performance. In particular it was found that anxiety levels were lowered and spatial memory was improved. In a preferred embodiment, particularly spatial memory was greatly and/or significantly improved. In another preferred embodiment, also social interaction was greatly and/or significantly improved.

Additionally, the inventors found that mice sensitized to ovalbumin (OVA) as a model for food allergy or atopy, the mice previously exposed to the allergen demonstrated higher anxiety levels and impaired spatial memory compared to control mice even though at the moment of testing itself no allergen exposure was applied. Furthermore, expression of brain derived neurotrophic factor (BDNF) messenger RNA (mRNA) and p-glycoprotein in the hippocampus was increased in the mice previously exposed to allergen. FACS analysis of the homogenized hippocampal cells of these animals revealed elevation in OVA-induced $CD11c^+F4/80^+$ $CD68^-$ macrophages. The increased macrophage levels observed in the brains of OVA-allergic mice originate from the circulation, which, in combination with observed decrease in brain blood barrier, implicate a role for periphery-driven monocytes in inducing the decrease in brain function observed in the allergic mice. The present data show that allergy- or atopy-dependent peripheral inflammation modifies the brain inflammatory status and dampens the cognitive abilities of the animals, indicating that allergy plays a role in the development and/or progression of neurological disorders such as cognitive and behavioral abnormalities, and neuroinflammation. So, to the best of our knowledge for the first time, it was demonstrated that subjects suffering from allergy or atopy have symptoms similar to an impaired gut brain axis.

It was found that the OVA-induced aberrant cognitive, behavioral and molecular changes were returned to levels observed in non allergic control mice upon dietary supplementation with *Bifidobacterium breve* in combination with non-digestible oligosaccharides (synbiotics), showing that in allergic mice this dietary intervention resulted in an even more prominent improvement of cognitive and behavioral function. In addition, the elevated OVA-induced $CD11c^+F4/80^+CD68^-$ macrophages, were attenuated by the synbiotic treatment. Synbiotic treatment resulted in elevated $CD11b^+CD68^+F4/80^{low}$ cells.

Using a mice model with dextran sodium sulfate (DSS) to induce intestinal inflammation it was found that the DSS exposed mice demonstrated higher anxiety levels and impaired spatial memory, while the locomotor activity was not affected. The intervention with synbiotics attenuated these effects to a much larger extent than could be expected based on the anti-inflammatory effect of the synbiotics alone. Furthermore the data indicate that the synbiotic composition is more effective than the *B. breve* or non-digestible oligosaccharides alone.

Therefore the use of *B. breve* together with non-digestible oligosaccharides is particularly suitable to improve cognitive and behavioral performance in infants and young children, in particular infants with an age of 6 months or below, preterm infants, small for gestational age (SGA) infant, infants born via caesarian section, infants and young children suffering from or being at risk of allergy and infants and young children suffering from intestinal inflammation.

Further, the inventors found that a cow's milk allergy (CMA) model is associated with disturbed social interaction and impaired spatial memory, the mice previously sensitized to whey protein demonstrated less social interaction and lesser spatial memory compared to non-allergic control mice. These observations underscore the effects of allergy on cognitive and behavioral performance as addressed in the models above. For mice which had been supplemented with *Bifidobacterium breve*, non-digestible oligosaccharides (synbiotics) and glutamine, social interaction and alternation or spatial memory levels were improved to levels comparable as for non-allergic mice. Therefore the use of *B. breve* together with non-digestible oligosaccharides and glutamine is particularly suitable to improve cognitive and behavioral performance, particularly to improve spatial memory and/or social interaction, in infants and young children, in particular infants with an age of 6 months or below, preterm infants, small for gestational age (SGA) infant, infants born via caesarian section, infants and young children suffering from or being at risk of allergy and infants and young children suffering from intestinal inflammation.

Also, data are herein also presented that interestingly show that nutritional supplementation of normal, non-allergic mice with a diet comprising *Bifidobacterium breve*, non-digestible oligosaccharides (synbiotics) with or without glutamine, leads to an improvement in social interaction, and that supplementation of the diet with *Bifidobacterium breve*, non-digestible oligosaccharides (synbiotics) and glutamine leads to significantly improved spatial memory performance.

The present invention further relates to a kit-of-parts suitable for feeding preterm infants comprising or consisting of the following two, three, four or five different containers and instructions for use, meaning said kit of parts comprises or consists of a first container comprising glutamine, fructo-oligosaccharides (FOS) and galacto-oligosaccharides (GOS), and a second container comprising *Bifidobacterium breve*. Preferably, said kit of parts also contains a one or more additional containers comprising a protein supplement, a human milk fortifier and/or a preterm infant formula. The kit preferably comprises instructions for use of the kit of parts for feeding preterm infants.

DETAILED DESCRIPTION OF THE INVENTION

The present invention thus concerns a method for improving cognitive performance, cognitive development, behavioral performance behavioral development and/or social interaction in an infant or toddler, comprising administering to the infant or toddler a nutritional composition comprising *Bifidobacterium breve* and comprising at least one non digestible oligosaccharide selected from the group consisting fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides.

The invention can also be worded as the use of *Bifidobacterium breve* and at least one non digestible oligosaccharide selected from the group consisting fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides, or a composition comprising *Bifidobacterium breve* and the at least one non digestible oligosaccharide, for the manufacture of a nutritional composition for improving cognitive performance, cognitive development, behavioral performance, behavioral development and/or social interaction in an infant or toddler. In one aspect, the invention particularly relates to improving cognitive performance, preferably involving memory performance, preferably spatial memory performance. Also, the invention particularly relates to improving social interaction.

The invention can also be worded as a nutritional composition comprising *Bifidobacterium breve* and comprising at least one non digestible oligosaccharide selected from the group consisting fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides for use in improving cognitive performance, cognitive development, behavioral performance, behavioral development and/or social interaction in an infant or toddler. In one aspect, the invention particularly relates to improving cognitive performance, preferably involving memory performance, preferably spatial memory performance. Also, the invention particularly relates to improving social interaction.

In a preferred embodiment of the present method or use, the infant or toddler is selected from the group consisting of infants with an age of 6 months or below, preterm infants, small for gestational age (SGA) infant, infants born via caesarian section, infants or toddlers suffering from allergy or infants or toddlers being at risk of allergy and infants or toddlers suffering from intestinal inflammation. In a preferred embodiment of the present method or use is for providing nutrition to the infant or toddler.

The invention also concerns a method for treating or preventing decreased cognitive performance, decreased cognitive development, decreased behavioral performance, decreased behavioral development, decreased social interaction and/or neuroinflammation, preferably decreased cognitive performance, preferably decreased memory performance, preferably decreased spatial memory performance, and preferably decreased social interaction, in an infant or toddler selected from the group consisting of infants or toddlers suffering from allergy, infants or toddlers being at risk of allergy, infants or toddlers suffering from intestinal inflammation, and preterm infants, said method comprising administering to the infant or toddler a nutritional composition comprising *Bifidobacterium breve* and comprising at least one non digestible oligosaccharide selected from the group consisting fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides.

The invention can also be worded as the use of *Bifidobacterium breve* and at least one non digestible oligosaccharide selected from the group consisting fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides, or a composition comprising *Bifidobacterium breve* and the at least one non digestible oligosaccharide, for the manufacture of a nutritional composition for treating or preventing decreased cognitive performance, decreased cognitive development, decreased behavioral performance, decreased behavioral development, decreased social interaction and/or neuroinflammation, preferably decreased cognitive performance, preferably decreased memory performance, preferably decreased spatial memory performance, and preferably decreased social interaction, in an infant or toddler selected from the group consisting of infants with an age of 6 months or below, preterm infants, small for gestational age (SGA) infant, infants born via caesarian section, infants or toddlers suffering from allergy or infants or toddlers being at risk of allergy and infants or toddlers suffering from intestinal inflammation.

The invention can also be worded as a nutritional composition comprising *Bifidobacterium breve* and comprising at least one non digestible oligosaccharide selected from the group consisting fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides for use intreating or preventing decreased cognitive performance, decreased cognitive development, decreased behavioral performance, decreased behavioral development, decreased social interaction and/or neuroinflammation, preferably decreased cognitive performance, preferably decreased memory performance, preferably decreased spatial memory performance, and preferably decreased social interaction, in an infant or toddler selected from the group consisting of infants with an age of 6 months or below, preterm infants, small for gestational age (SGA) infant, infants born via caesarian section, infants or toddlers suffering from allergy or infants or toddlers being at risk of allergy and infants or toddlers suffering from intestinal inflammation.

In a preferred embodiment of the present method or use is for providing nutrition to the infant or toddler selected from the group consisting of infants with an age of 6 months or below, preterm infants, small for gestational age (SGA) infant, infants born via caesarian section, infants or toddlers suffering from allergy or infants or toddlers being at risk of allergy and infants or toddlers suffering from intestinal inflammation.

The invention also concerns a method for feeding or a method of providing nutrition to an infant or toddler selected from the group consisting of infants with an age of 6 months or below, preterm infants, small for gestational age (SGA) infant, infants born via caesarian section, infants or toddlers suffering from allergy or infants or toddlers being at risk of allergy and infants or toddlers suffering from intestinal inflammation comprising administering a nutritional composition comprising a) *Bifidobacterium breve*, b) at least one non digestible oligosaccharide selected from the group consisting fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic uronic acid oligosaccharides, c) glutamine in the form of free amino acids and/or glutamine containing dipeptide and/or glutaime containing tripeptide and preferably d) LC-PUFA in the form or arachidonic acid and/or docosahexaenoic acid.

In other words the invention concerns the use of a nutritional composition comprising a) *Bifidobacterium breve*, b) at least one non digestible oligosaccharide selected from the group consisting fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic uronic acid oligosaccharides, c) glutamine in the form of free amino acids and/or glutamine containing dipeptide and/or glutaime containing tripeptide and d) LC-PUFA in the form or arachidonic acid and/or docosahexaenoic acid for providing nutrition to an to an infant or toddler selected from the group consisting of infants with an age of 6 months or below, preterm infants, small for gestational age (SGA) infant, infants born via caesarian section, infants or toddlers suffering from allergy or infants or toddlers being at risk of allergy and infants or toddlers suffering from intestinal inflammation.

The invention can also be worded as a nutritional composition comprising a) *Bifidobacterium breve*, b) at least one non digestible oligosaccharide selected from the group consisting fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic uronic acid oligosaccharides, c) glutamine in the form of free amino acids and/or glutamine containing dipeptide and/or glutaime containing tripeptide and preferably d) LC-PUFA in the form or arachidonic acid and/or docosahexaenoic acid for use in providing nutrition to an to an infant or toddler selected from the group consisting of infants with an age of 6 months or below, preterm infants, small for gestational age (SGA) infant, infants born via caesarian section, infants or toddlers suffering from allergy or infants or toddlers being at risk of allergy and infants or toddlers suffering from intestinal inflammation.

Preferably the composition comprises
a) *Bifidobacterium breve* in an amount of $10^2$ to $10^{13}$ cfu per g dry weight of the nutritional composition,
b) at least one non digestible oligosaccharide selected from the group consisting fructo-oligosaccharides, galacto-oligosaccharides, in an amount of 0.5 to 20 wt. % based on dry weight of the nutritional composition,
c) glutamine in the form of free amino acids and/or glutamine containing dipeptide and/or glutaime containing tripeptide in an amount of at least 1.5 wt. % based on dry weight of the nutritional composition, and preferably
d) LC-PUFA in the form or arachidonic acid and/or docosahexaenoic acid.

Also the invention concerns a nutritional composition comprising protein, fat and digestible carbohydrate and further comprising
a) *Bifidobacterium breve* in an amount of $10^2$ to $10^{13}$ cfu per g dry weight of the nutritional composition,
b) at least one non digestible oligosaccharide selected from the group consisting fructo-oligosaccharides, galacto-oligosaccharides, in an amount of 0.5 to 20 wt. % based on dry weight of the nutritional composition,
c) glutamine in the form of free amino acids and/or glutamine containing dipeptide and/or glutaime containing tripeptide in an amount of at least 1.5 wt. % based on dry weight of the nutritional composition, and preferably
d) LC-PUFA in the form or arachidonic acid and/or docosahexaenoic acid.

*Bifidobacterium breve*

The present composition comprises *Bifidobacterium breve*. *Bifidobacterium breve* is a Gram-positive, anaerobic, branched rod-shaped bacterium. The *B. breve* preferably has at least 95% identity of the 16 S rRNA sequence when compared to the type strain of *B. breve* ATCC 15700, more preferably at least 97% identity (Stackebrandt & Goebel, 1994, *Int. J. Syst. Bacteriol.* 44:846-849). Preferred *B. breve* strains are those isolated from the faeces of healthy human milk-fed infants. Typically, these are commercially available from producers of lactic acid bacteria, but they can also be directly isolated from faeces, identified, characterized and produced. According to a preferred embodiment, the present composition contains at least one *B. breve* selected from the group consisting of *B. breve* Bb-03 (Rhodia/Danisco), *B. breve* M-16V (Morinaga), *B. breve* R0070 (Institute Rosell, Lallemand), *B. breve* BR03 (Probiotical), *B. breve* BR92) (Cell Biotech), DSM 20091, LMG 11613, YIT4065, FERM BP-6223 and CNCM I-2219. Most preferably, the *B. breve* is selected from the group consisting of *B. breve* M-16V and *B. breve* CNCM I-2219, most preferably M-16V. *B. breve* 1-2219 was published in WO 2004/093899 and was deposited at the Collection Nationale de Cultures de Microorganisms, Institute Pasteur, Paris, France on 31 May 1999 by Compagnie Gervais Danone. *B. breve* M-16V was deposited as BCCM/LMG23729 and is commercially available from Morinaga Milk Industry Co., Ltd.

The present composition preferably contains $10^2$ to $10^{13}$ colony forming units (cfu) *B. breve* per gram dry weight of the present composition, preferably $10^4$ to $10^{12}$, more preferably $10^5$ to $10^{10}$, most preferably from $10^5$ to $1\times10^8$ cfu *B. breve* per gram dry weight of the present composition. The dose of *B. breve* according to the present invention is preferably administered at a daily dose of $10^2$ to $10^{13}$, more preferably from $10^5$ to $10^{12}$, most preferably from $10^7$ to $5\times10^9$ colony forming units (cfu). Preferably the composition comprises $10^3$ to $10^{13}$ cfu *B. breve* per 100 ml, more preferably $10^6$ to $10^{11}$ cfu *B. breve* per 100 ml, most preferably $10^7$ to $10^9$ cfu *B. breve* per 100 ml.

The present composition preferably comprises viable *B. breve*. Alternatively, the present composition preferably comprises non-viable *B. breve* equivalent to the amounts of cfu as described above. The equivalent of cfu can be determined by performing the 5'nuclease assay with the *B. breve* probes and primers as disclosed in WO 2005/039319 in the product (i.e. an infant formula) comprising non-viable *B. breve* and compare this with a calibration curve obtained from a comparable product (for instance a standard infant formula) to which known amounts in cfu of viable, preferably dried, *B. breve* have been added. The dried viable bifidobacteria can be commercially obtained as described above. *B. breve* cells can be made non-viable by methods known in the art, including heat treatment steps (including sterilization, pasteurization, UHT treatment), radiation (UV), treatment with oxygen, treatment with bactericidals such as ethanol, sonication, ultra high pressure application, high pressure homogenization and use of a cell disruptor. Preferably the *B. breve* is heat-killed. The presence of non-viable *B. breve* advantageously provides many product technological benefits, including increased shelf-life, a reduced incidence of bacterial contamination, decreased post-acidification of the product, improved dosage control and improved convenience of reconstitution. Consumption of inactivated *B. breve* also show advantageous effects in reducing allergy and inflammation.

Non-Digestible Oligosaccharides

The present composition comprises non-digestible oligosaccharides (NDO). The term "oligosaccharide" as used in the present invention preferably refers to a saccharide with a degree of polymerization (DP) of 2 to 250, preferably a DP of 2 to 100, more preferably of 2 to 60. It is understood that in the context of this invention a saccharide with a DP in a certain range may include a mixture of saccharides with different average DP's, for example, if an oligosaccharide with a DP of 2 to 100 is included in the present composition, this may include compositions which contain oligosaccharides with an average DP between 2 and 5, an average DP between 50 and 70 and an average DP between 7 and 60. The term "non-digestible oligosaccharide" as used in the present invention refers to oligosaccharides which are not or only partially digested in the intestine by the action of acids or digestive enzymes present in the human upper digestive tract (small intestine and stomach) but which are fermented by the human intestinal flora. For example, sucrose, lactose, maltose and maltodextrins are considered digestible. For example, galacto-oligosaccharides, fructo-oligosaccharides are considered non-digestible oligosaccharide.

The non-digestible oligosaccharide is selected from the group consisting of fructo-oligosaccharides (such as inulin), galacto-oligosaccharides (such as transgalacto-oligosaccharides or beta-galacto-oligosaccharides), gluco-oligosaccharides (such as gentio-, nigero- and cyclodextrin-oligosaccharides), arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides. In one embodiment, the present nutritional composition comprises of 0.5 to 20 wt. % non-digestible oligosaccharides per g dry weight of the nutritional composition.

Preferably the present composition comprises fructo-oligosaccharides and/or galacto-oligosaccharides, more preferably galacto-oligosaccharides, most preferably transgalacto-oligosaccharides. In a preferred embodiment the composition comprises a mixture of transgalacto-oligosaccharides and fructo-oligosaccharides. Preferably the present composition comprises galacto-oligosaccharides with a DP of 2-10, preferably with an average DP between 2 and 10, and/or fructo-oligosaccharides with a DP of 2-60, preferably with an average DP between 2 and 60, preferably with an average DP between 10 and 60, preferably with an average DP between 20 and 60. In one embodiment the present composition comprises galacto-oligosaccharides with a DP of 2-10, preferably with an average DP between 2 and 10, and/or fructo-oligosaccharides with a DP of 2-10, preferably with an average DP between 2 and 10. Preferably the composition comprises galacto-oligosaccharides and fructo-oligosaccharides in a weight ratio of 20 to 0.5, more preferably 20 to 1, most preferably from 12 to 2.

The galacto-oligosaccharide is preferably selected from the group consisting of transgalacto-oligosaccharides, lacto-N-tetraose (LNT), lacto-N-neotetraose (neo-LNT), fucosyl-lactose, fucosylated LNT and fucosylated neo-LNT. In a particularly preferred embodiment the present method comprises the administration of transgalacto-oligosaccharides ([galactose]$_n$-glucose; wherein n is an integer between 1 and 60, i.e. 2, 3, 4, 5, 6, . . . . . , 59, 60; preferably n is selected from 2, 3, 4, 5, 6, 7, 8, 9, or 10). Transgalacto-oligosaccharides (TOS) are for example sold under the trademark Vivinal™ (Borculo Domo Ingredients, Netherlands). Preferably the saccharides of the transgalacto-oligosaccharides are β-linked.

In one embodiment the present composition preferably contains fructooligosaccharide. The term "fructo-oligosaccharide" as used herein refers to a non-digestible polysaccharide comprising a chain of at least 2β-linked fructose units, with a DP of 2 to 250, preferably 7 to 100, more preferably 20 to 60. In one embodiment preferably inulin is used. Inulin is for example available under the tradename "Raftilin HP®", (Orafti). The average DP of the present fructo-oligosaccharide is preferably at least 7, more preferably at least 10, preferably below 100. The fructo-oligosaccharide used preferably has the (majority of) fructose units linked with a β(2→1) linkage. Other terms for fructooligosaccharides include inulin, fructopolysaccharide, polyfructose, fructans and oligofructose. The present composition preferably comprises fructo-oligosaccharides with a DP of 2 to 200, preferably 7 to 100, more preferably 20 to 60. In one embodiment the present nutritional composition preferably comprises 2 different fractions of fructo-oligosaccharides, one fraction with an average DP between 2 and 20 and a second fraction with an average DP between 20 and 60, or one fraction with an average DP between 2 and 10 and a second fraction with an average DP between 10 and 60. Preferably, the composition comprises of 80 mg to 2 g non-digestible oligosaccharides per 100 ml, more preferably 150 mg to 1.50 g, even more preferably 300 mg to 1 g per 100 ml. Based on dry weight, the composition preferably comprises 0.25 wt. % to 20 wt. %, more preferably 0.5 wt. % to 10 wt. %, even more preferably 1.5 wt. % to 7.5 wt. % non-digestible oligosaccharides. Preferably the composition comprises $10^2$ to $10^{13}$ cfu *B. breve* per gram and 0.25 wt. % to 20 wt. % non-digestible oligosaccharides based on dry weight, more preferably $10^5$ to $10^{10}$ cfu *B. breve* per gram and 0.5 wt. % to 10 wt. % non-digestible oligosaccharides based on dry weight. Preferably the composition comprises $10^3$ to $10^{13}$ cfu *B. breve* and 80 mg to 2 g non-digestible oligosaccharides per 100 ml, more preferably $10^6$ to $10^{11}$ cfu *B. breve* and 300 mg to 1 g non-digestible oligosaccharides per 100 ml.

Preferably the nutritional composition comprises i) $1\times10^5$ cfu to $1\times10^{10}$ cfu *B. breve* per g dry weight, more preferably $1\times10^6$ cfu to $1\times10^{10}$ cfu; and either ii) 0.5 to 20 wt. % galacto-oligosaccharides based on dry weight, more preferably 0.5 to 10 wt. % galacto-oligosaccharides or iii) 0.05 to 2% fructo-oligosaccharides based on dry weight, more preferably 0.1 to 1 wt. % fructo-oligosaccharides or both ii) and iii).

Glutamine

The nutritional composition of the present invention preferably comprises glutamine. Throughout this description this is also referred to as nutritional composition comprising glutamine or glutamine enriched nutritional composition. Glutamine in the present invention refers to L-glutamine. Glutamine is one of the most abundant amino acids in plasma and human milk and is considered conditionally essential in preterm infants. Glutamine is utilized as a source of energy and for nucleotide synthesis in all rapidly dividing cells, such as the intestinal lining and certain immune cells. In the brain, glutamine is a substrate for neurotransmitters and an important source of energy for the nervous system. Glutamine, together with the *Bifidobacterium breve* and non digestible oligosaccharides advantageously has a further improved, or synergistic effect, on cognitive performance, behavior, allergy, prevention of neuroinflammation and/or intestinal inflammation. Infants with an age of 6 months or below, preterm infants, small for gestational age (SGA) infant, infants born via caesarian section, infants or toddlers suffering from allergy or infants or toddlers being at risk of allergy and infants or toddlers suffering from intestinal inflammation may be especially susceptible to glutamine depletion as nutritional supply of glutamine is limited in the first weeks after birth. Furthermore the endogenous capacity to synthesize glutamine from glutamate may be compromised in these infants and in particular is not fully developed in preterm and SGA infants.

Glutamine is preferably present in an easily absorbable form. Because of the immaturity of the intestinal tract of the SGA and/or preterm infant, glutamine present in intact protein is less easily absorbed. Therefore the glutamine is preferably present in the form of free amino acids and/or di- and tripeptides comprising glutamine, most preferably glutamine comprising dipeptide and/or free glutamine. Free glutamine and glutamine comprising dipeptide and glutamine comprising tripeptide are commercially available, for example at Ajinomoto, USA. In one embodiment, the nutritional composition of the present invention comprises less than 0.3 g/l arginine-glutamine dipeptide, when the composition is in liquid form, or less than 2.5 wt. %, preferably less than 1.5 wt. %, more preferable less than 1 wt. %, even more preferably less than 0.5 wt. % arginine-glutamine dipeptide based on dry weight of the composition. In one embodiment, the nutritional composition of the present invention does not comprise arginine-glutamine dipeptide.

The nutritional composition of the present invention preferably comprises glutamine levels higher then normally present in human milk protein or standard preterm formula based on cow's milk derived protein. Preferably the nutritional composition of the present invention comprises at least 12 wt. %, more preferably at least 15 wt. %, even more preferably at least 30 wt. % glutamine based on total protein. Preferably the nutritional composition of the present invention comprises at least 1.5 wt. %, more preferably at least 2 wt. %, even more preferably at least 4 wt. % glutamine based on dry weight of the nutritional composition. Preferably the nutritional composition of the present invention comprises at least 0.3 g, more preferably at least 0.5 g, even more preferably at least 1 g glutamine based on 100 kcal. Preferably the composition of the present invention comprises at least 0.4 g, more preferably at least 0.6 g, even more preferably at least 1.25 g glutamine per 100 ml. Preferably the nutritional composition of the present invention comprises at least 12 wt. %, more preferably at least 15 wt. %, even more preferably at least 30 wt. % glutamine in the form of free amino acid and if present glutamine containing dipeptide and glutamine containing tripeptide based on total protein. Preferably the nutritional composition of the present invention comprises at least 1.5 wt. %, more preferably at least 2 wt. %, even more preferably at least 4 wt. % glutamine in the form of free amino acid, and if present, glutamine containing dipeptide and glutamine containing tripeptide, based on dry weight of the nutritional composition. Preferably the nutritional composition of the present invention comprises at least 0.3 g, more preferably at least 0.5 g, even more preferably at least 1 g glutamine in the form of free amino acid, and if present, glutamine containing dipeptide and glutamine containing tripeptide, based on 100 kcal.

Preferably the present nutritional composition comprising glutamine is in dry form, preferably a powder. This powder is suitable for reconstitution with water or another aqueous phase. When glutamine is in powder form it advantageously has a better shelf life. Glutamine, in particular free glutamine and glutamine dipeptide, is more stable when stored in dry form.

LC-PUFA

Preferably the present composition comprises long chain poly unsaturated fatty acids (LC-PUFA), more preferably n-3 and n-6 LC-PUFA, even more preferable arachidonic acid (ARA) and docosahexaenoic acid (DHA). LC-PUFA is an important part of the fatty acyl chain composition of the brain membranes and therefore advantageously improves cognitive and behavioral performance or development and prevents neuroinflammation. The presence of LC-PUFA, in particular ARA and DHA, will have a further improved, or even synergistic, beneficial effect together with *B. breve* and non-digestible oligosaccharides n-3 LC-PUFA, in particular docosahexaenoic acid (DHA), is an important part of the fatty acyl chain composition of the brain membranes and advantageously improves cognitive and behavioral performance or development. More preferably, the present composition comprises n-3 LC-PUFA, even more preferably DHA. Since a low concentration of DHA is already effective, the content of n-3 LC-PUFA in the present composition, preferably does not exceed 15 wt. % of the total fatty acid content, preferably does not exceed 10 wt. %, even more preferably does not exceed 5 wt. %. Preferably the present composition comprises at least 0.2 wt. %, preferably at least 0.5 wt. %, more preferably at least 0.75 wt. % n-3 LC-PUFA of the total fatty acid content. The DHA content preferably does not exceed 5 wt. %, more preferably does not exceed 1 wt. %, but is preferably at least 0.1 wt. % of the total fatty acid. Preferably as a source of n-3 LC-PUFA single cell oil, preferably algal oil, fungal oil and/or microbial oil is used, since these oil sources have a low EPA/DHA ratio, which results in an improved effect on the brain. More preferably the present composition comprises fish oil, more preferably tuna oil.

n-6 LC-PUFA, in particular arachidonic acid (ARA) is an important part of the fatty acyl chain composition of the brain membranes and advantageously improves cognitive and behavioral performance or development. The present composition preferably comprises relatively low amounts of ARA. The n-6 LC-PUFA content preferably does not exceed 5 wt. %, more preferably does not exceed 0.8 wt. %, more preferably does not exceed 0.75 wt. %, even more preferably does not exceed 0.5 wt. % based on total fatty acids. Since ARA is important in infants for optimal functional membranes, especially membranes of neurological tissues, the amount of n-6 LC-PUFA is preferably at least 0.02 wt. %, more preferably at least 0.05 wt. %, even more preferably at least 0.1 wt. % based on total fatty acids, more preferably at least 0.25 wt. %.

The weight ratio n-6 LC-PUFA/n-3 LC-PUFA, in particular the weight ratio of ARA/DHA in the present infant nutrition is preferably from 3 to 0.5, more preferably from 2 to 1. Preferably the weight ratio is above 1. These ratio's ensure an optimal brain functioning.

LC-PUFA are preferably provided as free fatty acids, in triglyceride form, in diglyceride form, in monoglyceride form, in phospholipid form, or as a mixture of one of more of the above. Preferably the present composition contains LC-PUFA in triglyceride and/or phospholipid form, even more preferably phospholipid form since LC-PUFA in phospholipid form are better incorporated into membranes.

Therefore a dietary source of LC-PUFA in the form of phospholipids will have a further improved effect on the brain than when administered in form of triglycerides. A preferred source of LC-PUFA therefore is egg phospholipid. Commercial sources of egg oil, rich in phospholipids, and having arachidonic and docosahexaenoic fatty acyl chains in the phospholipid molecules are known.

Compositions

The present invention advantageously concerns a composition wherein the lipid provides 5 to 50% of the total calories, the protein provides 5 to 50% of the total calories, and the carbohydrate provides 15 to 90% of the total calories. Preferably, in the present composition the lipid provides 35 to 50% of the total calories, the protein provides 7.5 to 12.5% of the total calories, and the carbohydrate provides 40 to 55% of the total calories. For calculation of the % of total calories for the protein component, the total of energy provided by the proteins, peptides and amino acids needs to be taken into account.

The present composition preferably comprises at least one lipid selected from the group consisting of animal lipid (excluding human lipids) and vegetable lipids. Preferably the present composition comprises a combination of vegetable lipids and at least one oil selected from the group consisting of fish oil, animal oil, algae oil, fungal oil, and bacterial oil. The present composition comprising non-digestible oligosaccharides and B. breve excludes human milk.

The present composition preferably comprises protein. The protein component used in the nutritional preparation are preferably selected from the group consisting of non-human animal proteins (preferably milk proteins, preferably proteins from cow's milk), vegetable proteins (preferably soy protein and/or rice protein), free amino acids and mixtures thereof. The present composition preferably contains casein, whey, hydrolyzed casein and/or hydrolyzed whey protein. Preferably the protein comprises intact proteins, more preferably intact bovine whey proteins and/or intact bovine casein proteins. As the present composition is preferably suitably for use by infants suffering from or at risk of allergy, the protein is preferably selected from the group consisting of hydrolyzed milk protein, more preferably hydrolyzed whey protein. As the present composition is preferably suitably for use by preterm or SGA infants, the protein is preferably selected from the group consisting of hydrolyzed milk protein, more preferably selected from the group consisting of hydrolyzed whey protein and hydrolyzed casein.

The present composition preferably comprises digestible carbohydrates. The present composition preferably comprises a digestible carbohydrate component, wherein at least 35 wt. %, more preferably at least 50 wt. %, more preferably at least 75 wt. %, even more preferably at least 90 wt. %, most preferably at least 95 wt. % is lactose. The present composition preferably comprises at least 25 grams lactose per 100 gram dry weight of the present composition, preferably at least 40 grams lactose/100 gram.

The liquid nutritional composition preferably has a caloric density between 0.1 and 2.5 kcal/ml, even more preferably a caloric density of between 0.5 and 1.5 kcal/ml, most preferably between 0.6 and 0.8 kcal/ml. The amount of nutritional composition administered per day is preferably between 50 and 2000 ml, more preferably between 200 and 1500, most preferably between 400 and 1000 ml.

In one embodiment the nutritional composition of the present invention is a preterm formula. The preterm formula comprises all macro- and micronutrients needed for preterm or SGA infants so as to achieve a growth similar to fetal growth coupled with satisfactory functional development.

In a preferred embodiment the preterm formula comprises from 5 to 25 wt. % protein, preferably 9 to 20 wt. %, more preferably 13 to 18 wt. % protein based on the dry weight of the preterm formula. In a preferred embodiment the preterm formula comprises from 1.8 to 3.0 g protein, preferably, preferably 2.0 to 3.0 g, preferably 2.5 g to 2.6 g protein, per 100 ml.

Preferably the preterm formula of the present invention comprises at least 12 wt. %, more preferably at least 15 wt. %, even more preferably at least 30 wt. % glutamine based on total protein. Preferably the preterm formula of the present invention comprises no more than 80 wt. %, more preferably no more than 50 wt. % glutamine based on total protein. Preferably the preterm formula of the present invention comprises at least 1.5 wt. %, more preferably at least 2 wt. %, even more preferably at least 4 wt. % glutamine based on dry weight of the preterm formula. Preferably the preterm formula of the present invention comprises no more than 20 wt. %, more preferably no more than 10 wt. % glutamine based on dry weight of the preterm formula. Preferably the nutritional composition of the present invention comprises at least 0.3 g, more preferably at least 0.5 g, even more preferably at least 1 g glutamine based on 100 kcal of the preterm formula. Preferably the preterm formula of the present invention comprises no more than 5 g, even more preferably no more than 2 g glutamine based on 100 kcal of the preterm formula.

The preterm formula of the present invention in ready to drink form has in a preferred embodiment about 70 to 90 kcal, preferably 75 to 85 kcal per 100 ml.

Preferably the preterm formula has an osmolarity below 450 mOsmol/l, more preferably below 400, even more preferably below 350. Particularly in preterm infants, a too high osmolarity is a disadvantage.

In one embodiment the present invention concerns a supplement, suitable to fortify human milk, to fortify human milk fortified with a standard human milk fortifier or to fortify a standard preterm formula. In the context of this invention, a supplement does not comprise all macro- and micronutrients needed for preterm infants so as to achieve a growth similar to fetal growth coupled with satisfactory functional development.

In one embodiment the nutritional composition of the present invention is a post discharge formula. The post discharge formula comprises all macro- and micronutrients needed for preterm infants so as to achieve a growth similar to fetal growth coupled with satisfactory functional development.

Thus in one embodiment the nutritional composition according to the present invention or for use according to the present invention comprises protein, fat and/or digestible carbohydrates and is selected from the group consisting of an infant starter formula, an infant follow on formula, a toddler milk, a preterm formula, a post discharge formula and a human milk fortifier.

In a particular embodiment, the present invention relates to a kit-of-parts suitable and intended for feeding preterm infants comprising or consisting of up to five different containers each with different contents and instructions for use. Said kit of parts comprises or consists of a first container comprising glutamine, preferably in the form of free amino acids, dipeptides and/or tripeptides, and at least one non-digestible oligosaccharide selected from the group consisting of fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides, more preferably a combination of at least fructo-oligosaccharide (FOS) and galacto-oligosaccharides (GOS), and a second container comprising *Bifidobacterium breve*.

Preferably, said kit of parts also includes one or more containers comprising a (protein) supplement suitable to fortify human milk, or to fortify human milk fortified with a standard human milk fortifier or a protein supplement to fortify a standard preterm formula. Such supplements do not comprise all macro- and micronutrients needed for preterm infants so as to achieve a growth similar to fetal growth coupled with satisfactory functional development.

In a preferred embodiment, the first container of the kit of parts comprises glutamine in free amino acid form, as a glutamine dipeptide, as a glutamine tri-peptide and/or an arginine-glutamine dipeptide, with fructo-oligosaccharide (FOS or 1cFOS) and galacto-oligosaccharides (GOS or scGOS) present as well. GOS and FOS could be used as described elsewhere in the specification. The weight ratio of glutamine to the sum of non-digestible oligosaccharides GOS and FOS preferably lies between 2:1 and 1:4, more preferably lies between 1:1 and 1:3, most preferably lies around 1:2. Preferably said container is a sachet (or a bundle with from 2 to 100 individual sachets) or a tin can. Preferably, said glutamine/GOS/FOS is present in dry form, preferably in powdered form. In one embodiment, said first container contains glutamine/GOS/FOS in sterilized liquid form, more preferably in a concentrated form or as a daily unit dose to prevent spoilage.

In a preferred embodiment, the kit of parts comprises a container which comprises *Bifidobacterium breve* M16V, preferably as described above under the header "*Bifidobacterium breve*". Preferably said container is a sachet, or a bundle with from 2 to 100 individual sachets. Preferably, said *B. breve* is present in dry form, preferably in powdered form. Said container preferably comprises *B. breve* as a daily unit dose to prevent spoilage. The container preferably comprises $0.5 \times 10^9$ cfu to $1 \times 10^{10}$, preferably to be provided in a daily dose of between $1 \times 10^9$ cfu to $5 \times 10^9$ cfu. In one embodiment, the container preferably comprises $0.5 \times 10^9$ cfu to $1 \times 10^{10}$ preferably between $1 \times 10^9$ cfu to $5 \times 10^9$ cfu per g powder.

In a preferred embodiment, a container is included in the kit of parts that comprises a protein supplement which comprises at least 50% protein based on total calories of the protein supplement and/or at least 50 wt % protein based on dry weight of the protein supplement. Preferably, the protein supplement comprises at least 50% wt % protein, more preferable at least 60 wt % or at least 70 wt %, even more preferably at least 80 wt % protein based on dry weight of the protein supplement or based on total caloties of the protein supplement. The protein of the protein supplement preferably comprises or consists of (extensively) hydrolysed whey protein and/or hydrolysed casein protein. The protein supplement is preferably provided in dry form, such as a dry powder or as a sterilized liquid. It is preferably provided as a daily unit dose to prevent spoilage or in a tin can with a content of between 50 and 400 gram, more preferably between 100 and 300 gram. When present as a sterilized liquid, it is preferably present in a holder with a volume of between 4 and 100 mL.

Human milk may not always provide all the required nutrients to preterm infants, since human milk is intended to be consumed by term infants whereas preterm infants have increased nutritional requirements. Thus, in a preferred embodiment, a container is included in the kit of parts that comprises a fortifier to be used with human milk, i.e. a human milk fortifier (HMF). Said HMF may be provided in dry form, such as a dry powder. Preferably, the HMF has a caloric density of between 250 and 425 kcal/100 g powder, more preferably between 300 and 375 kcal/100 g powder. Preferably, the HMF has a protein content of between 20 and 40 En %, preferably comprising casein and/or whey protein, and preferably a carbohydrate content of between 50 and 80 En %, more preferably 60 and 75 En %. The HMF is preferably provided in a sachet or in a bundle of sachets, such as ranging from between 2 and 100 sachets or 25 to 75 sachets, with a content of between 1 and 5 gram. It is preferably provided as a daily unit dose to prevent spoilage.

The optional instructions for use of the kit of parts preferably contain instructions to use glutamine, GOS/FOS and *B. breve* expressed either in g/kg/day or g/100 mL ready-to-feed product, such as:

a) L-glutamine from 0.05 to 0.5 g/100 mL, preferably between 0.1 and 0.3 g/100 mL and GOS/FOS (preferably in a 9:1 weight ratio) from 0.1 to 1.0 g/100 mL, preferably from 0.2 to 0.6 g/100 mL, and/or, b) L-glutamine to be provided in a dose of 0.1 to 0.6 g/kg/day, preferably to be provided in a dose of 0.2 to 0.4 g/kg/day and GOS/FOS (preferably in a 9:1 weight ratio) to be provided in a dose of 0.2 to 1.2 g/kg/day, preferably to be provided in a dose of 0.4 to 0.8 g/kg/day, and c) *B. breve* to be provided in a daily dose of between $0.5*10^9$ cfu to $1*10^{10}$, preferably to be provided in a daily dose of between $1*10^9$ cfu to $5*10^9$ cfu. Preferably, the daily dose is to be divided equally over all individual feeding dosages given over the entire day.

In one embodiment, the invention relates to the use of the above kit for providing nutrition to preterm infants, particularly to achieve the effects as discussed here above and supported by the examples.

Application

The present method or use is specifically intended for infants and/or toddlers. Infants have an age of 0-12 months, toddlers have an age of 12-36 months.

The present composition is preferably enterally administered, more preferably orally. The present composition is preferably a nutritional formula, preferably an infant formula. The present composition can advantageously be applied as a complete nutrition for infants. The present composition preferably comprises lipid, protein, and carbohydrate and is preferably administered in liquid form. The present invention includes dry compositions, e.g. powders, which are accompanied with instructions as to admix said dry compositions, in particular nutritional formula, with a suitable liquid, e.g. water.

The present invention preferably relates to a method for feeding an infant selected from the group consisting of preterm (=premature) infants and very premature infants. Preterm infants are born before the end of the 37th week of pregnancy. Very preterm infants are born before the end of the 32th week of pregnancy. SGA infants are those whose birth weight lies below the 10th percentile for that gestational age. They have usually been the subject of intrauterine growth restriction (IUGR). Premature and/or SGA infants include low birth weight infants (LBW infants), very low birth weight infants (VLBW infants), and extremely low birth weight infants (ELBW infants). LBW infants are defined as infants with a weight less than 2500 g. VLBW infants as infants with a weight which is less than 1500 g, and ELBW infants as infants with a weight less than 1000 g.

The present inventions concerns improving cognitive performance, cognitive development, behavioral performance and/or behavioral development in an infant or toddler. In a preferred embodiment, the cognitive performance or cognitive development is memory performance or memory development, including spatial memory performance. In a preferred embodiment, the present invention concerns improving social interaction or improving social interaction behavior. In one aspect, the above effects are observed immediate upon administration, preferably within 24 months, more preferably within 12 months, more preferably with 6 months, most preferably withing 3 months. In yet a further embodiment the effect on cognitive performance and/or behavioral performance and/or neuroinflammation is observed later in life, when the human subject has an age of 36 months or above. Preferably at an age of 5 years and above. However, in one aspect such imprinting effects are not part of the invention.

Also the present inventions concerns treating or preventing (or reducing the risk of) decreased cognitive performance, decreased cognitive development, decreased behavioral performance, decreased behavioral development and/ or neuroinflammation in an infant or toddler selected from the group consisting of infants or toddlers suffering from allergy, infants or toddlers being at risk of allergy, infants or toddlers suffering from intestinal inflammation, and preterm infants. In a particularly preferred embodiment, the invention concerns treating or preventing (or reducing the risk of) decreased social interaction, decreased spatial memory and behavioural development or improving social interaction, spatial memory and/or behavioural development in an infant or toddler selected from the group consisting of infants or toddlers suffering from allergy, infants or toddlers being at risk of allergy, infants or toddlers suffering from intestinal inflammation, and preterm infants.

Hence the present invention provides a method for providing nutrition to a human infant and/or toddler, said method comprising administering to the infant and/or toddler the present composition. Preferably the infant and/or toddler has an age between 0 and 36 month, more preferably between 0 and 18 month, even more preferably between 0 and 12 months, most preferably between) and 6 months.

EXAMPLES

Example 1: Dietary Intervention with *B. breve* and Non Digestible Oligosaccharides Decreases Anxiety and May Improve Cognitive Performance C57B1/6 mice, were fed a control a control diet, *Bifidobacterium breve* M-16V of Morinaga (2% wt:wt $2\times10^9$ CFU/g; probiotic), GF (1% wt:wt, 9:1 scGOS:1cFOS; prebiotic) or a combination of both (GF/Bb) as described. Source of GOS; Vivinal-GOS, source of 1cFOS; RaftilinHP. Mice were fed the respective diet for about 3 weeks Locomotor activity of the animals was assessed at day 19 and 20 in a 250×250×200 mm arena. The light intensity was 20 lux at floor level. General locomotor activity was assessed to ensure animals were not physically affected by the DSS or OVA treatment. Locomotion of the animals was automatically tracked (TSE system, Germany). Time spent in the center of the open field is considered an anxiety measurement, and was automatically tracked. It can also be considered a measure for exploratory activity. Each animal was placed in the center of the open field and allowed to explore for 5 min, after which they were returned to their home cage.

Spatial working memory was assessed at day 19 and 20 using the T-maze paradigm. The procedure was adapted from Deacon and Rawlins, 2006. A trial consisted of two runs, with a time interval of 2 minutes. After the mouse had been released from the start arm, the animal was free to choose between both goal arms. As soon as the animal had entered one goal arm, the other goal arm was closed, where it was confined for 30 s by lowering the door of the goal arm. The animal was then returned to his home cage. After thoroughly cleaning the T-maze with 70% ethanol, the mouse was put back to the start arm and was free to choose one of the goal arms. The main measure was the alteration ratio, defined as proportion of trials on which alternation occurred (first to the left arm and then to the right arm or vice versa), divided by the total amount of trials. The percentage of spontaneous alternation was calculated from the alternation ratio multiplied by 100%. Total of 4 trials were conducted over one day.

In mice receiving the control diet the cognitive performance as measured in the T maze model (spatial memory), expressed as mean % of spontaneous alterations was about 78%. In the healthy mice receiving GF/Bb a slight increase was observed to about 80%.

With regard to behavioral performance (anxiety, expressed as mean time in s spend in center of an open field), in control diet fed mice this was about 95 s. Surprisingly in the healthy mice receiving GF/Bb a significant increase was observed compared to the control group (to about 121 s).

Example 2: Dietary Intervention with *B. breve* and Non Digestible Oligosaccharides Prevents Allergy-Induced Decreased Cognitive Performance, Anxiety and Neuroinflammation Three to four weeks old female specific pathogen free Balb/c mice (Charles River Laboratories, Maastricht, The Netherlands) were fed a control diet or a diet supplemented with *Bifidobacterium breve* M-16V (2% wt:wt, $2\times10^9$ CFU/g) and scGOS/1cFOS (1% wt:wt, 9:1 scGOS:1cFOS; GF/Bb diet) two weeks before and during oral sensitization to ovalbumin (OVA; Sigma). Mice were sensitized by administering 0.5 mL sterile PBS containing 20 ug/mL cholera toxin (CT) or 0.5 mL sterile PBS containing 20 ug/mL CT and 40 mg/mL OVA per oral gavage. Mice were sensitized once per week for five consecutive weeks. After sensitization, some mice received 10 ug OVA/100 uL sterile PBS i.d. in the ear pinnae to assess the acute allergic skin response 1 h after administration by measuring the ear thickness in duplicate using a digital micrometer (Mitutoyo, Veenendaal, The Netherlands). Ear swelling was corrected for basal ear thickness before injection. Mice were challenged by administering 100 mg OVA/0.5 mL sterile PBS per oral gavage. Faeces was collected 15-30 min. after challenge and water content was assessed.

Cognitive and behavioral performance was tested with the T maze and open field test as described in example 1. Furthermore nesting behavior was tested. Nesting behavior has been shown to depend on the intact hippocampal function. To assess the integrity of the hippocampal function of the OVA/DSS animals, a nesting building paradigm was performed. Effects of OVA/DSS and the corresponding treatments (i.e. synbiotics) were assessed in the nest construction abilities. Briefly, animals were provided with 2 pieces of paper towels overnight. Paper towel nest construction was scored the following morning (12 hours later) along a 4-point system: (0) no nesting: no noticeable evidence of material being touched; (1) poor nesting: part of the material manipulated or distributed over the cage, but still no nest site formed; (2) fair nesting: all the nesting material had been manipulated for nest building, but nest was flat—no presence of side walls; (3) efficient nesting; nest cup formulated, but side walls were not completely raised; (4) perfect nesting; nest site completely formed with the high and compact walls surrounding the nest hollow.

Mice were sacrificed 18 h after oral challenge and blood was collected in Minicollect® Z Serum Sep vials (Greiner). Blood was centrifuged for 30 min. at 14,000×g and sera were stored at −20° C.

After isolating and weighing hippocampi from the right hemisphere RNA was isolated from the hippocampus using the RNAeasy kit (Qiagen, Germantown, Md. USA) and, subsequently, reverse transcribed into cDNA using the iScript cDNA synthesis kit (BioRad, Hercules, Calif. USA). Real-time PCR was performed using iQ SYBR Green super mix kit (BioRad, Hercules, Calif. USA) with the CFX 96 Real-time system (BioRad, Hercules, Calif. USA). Expression levels were normalized against GAPDH and calculated using the delta-delta Ct method. The primers used were for GAPDH (F: GCATCCTGCACCACCAACTG, R: ACGCCACAGCTTTCCAGAGG) and BDNF (F: GAAGGCTGCAGGGGCATAGAC; R: TACACAGGAAGTGTCTATCCTTAT). Each sample was run in duplicate per gene of interest.

OVA-specific serum immunoglobulins were measured as known in the art. Microlon plates (Greiner) were coated with 100 mL 20 ug/mL OVA in carbonate/bicarbonate buffer, 0.05M, pH=9.6. Plates were blocked for 1 h with PBS/5% BSA. Next, samples were applied in multiple dilutions and incubated for 2 h, followed by incubation with biotinylated rat anti-mouse IgE, IgG1 or IgG2a (1 ug/mL; BD Biosciences) for 90 min. Plates were subsequently incubated for 1 h with streptavidin-horse radish peroxidase (0.5 ug/mL; Sanquin) and were developed using o-phenylendiamine. Reactions were stopped using 2M $H_2SO_4$ and optical density was measured at 490 nm. in a microplate reader (Bio-Rad).

Cells were collected and taken up in PBS/2% FCS. MoDC were characterized using CD16-PE(3G8; BD Biosciences), DC-SIGN-FITC(120507), CX3CR1-FITC (528728; both R&D Systems), CD14-PerCp-Cy5(61D3), CD40-FITC (5C3), CD80-PE(2D10.4), CD83-PE(HB15e), CD86-PE (1T2.2), CD103-APC(B-Ly7), HLA-DR-PE(LN3) or CD103-AlexaFluor®647(B-Ly7)(eBioscience) antibodies. CD4+ T cells were extracellularly stained using CD4-PerCP-Cy5.5(OKT-4) and CD25-AlexaFluor488(BC96) antibodies followed by fixation and permeabilization using the Foxp3 staining buffer set (eBioscience) according to manufacturer's protocol. T cells were intracellularly stained using Foxp3-PE (PCH101, eBioscience) antibodies. FITC-labelled mouse IgG2b, PE-labelled mouse IgG2b, PerCP-Cy5.5-labeled mouse IgG1 and eFluor®660-labelled mouse IgG1 antibodies were used as isotype controls(eBioscience). After staining, moDC were taken up in PBS/2% FCS, fixed with 2% paraformaldehyde and mean fluorescence intensity was measured. Mean fluorescence intensity was corrected for isotype background staining.

Statistics: All results were expressed as means±standard error (SEM) and differences among means were considered significant if the p value was equal to or less than 0.05. Nonparametric statistics (Kruskal-Wallis test) were applied to analyze passive avoidance latency times, T-maze spontaneous alteration, and nesting scores followed by post-hoc analysis using Dunn's multiple comparison test. Total activity in open field, histological, molecular and immunohistochemical data were analyzed using a two-way ANOVA followed by post hoc tests with Bonferonni correction.

Results

The protocol for ovalbumin allergy induction was effective as can be deduced from the effects on ear swelling and OVA-specific IgE levels in serum. Ear swelling was about 50 um in the control mice and was significantly higher, about 150 um, in the OVA sensitized mice. OVA sensitized mice consuming a diet of GF/Bb showed a significantly decreased earswelling of about 100 um.

OVA specific IgE was absent in the mice not sensitized to OVA. In the OVA sensitized mice receiving the control diet OVA specific IgE was observed (OD 490 nm about 0.91), whereas the mice with the GF/Bb diet it was significantly lower, about 0.33.

Diarrhea like symptoms, determined as water in the faces, was about 55% in the non-allergic mice, and the OVA allergic mice consuming the GF/Bb diet, whereas in the OVA allergic mice consuming the control diet feaces was significantly more watery (about 63%).

OVA challenge had no effect on the T-maze or open field latencies, compared to the control mice, suggesting the spatial memory impairments are independent of any potential aversive physical discomfort As can be deduced from the results shown in Table 1 the GF/Bb treatment attenuated the OVA induced decreased cognitive performance in a statistically significant way. It should be noted that the test was performed 1 week post sensitization, this was actually done to minimize any potential aversive effects when the acute allergic response had disappeared. Again also an very small increase effect was observed in healthy mice receiving the GF/Bb diet.

TABLE 1

| T maze test, % of alternation | | | | |
|---|---|---|---|---|
| | Control, control diet | Control, GF/Bb diet | OVA mice, control diet | OVA mice, GF/Bb diet |
| Mean | 78.25 | 79.75 | 54.20* | 79.33 |
| s.e. | 5.2 | 5.8 | 3.7 | 3.3 |

As can be deduced from the results shown in Table 2 the GF/Bb treatment attenuated the OVA induced increased anxiety level over 5 challenges in a statistically significant way. It should be noted that the open field test was again performed at time points 48 h post sensitization, this was actually done to minimize any potential aversive effects when the acute allergic response had disappeared. Again also an significant increased effect was observed in healthy mice receiving the GF/Bb diet.

TABLE 2

| open field time in center (s) | | | | |
|---|---|---|---|---|
| | Control, control diet | Control, GF/Bb diet | OVA mice, control diet | OVA mice, GF/Bb diet |
| Mean | 68.44 | 84.53 | 46.34* | 65.37 |
| s.e. | 5.1 | 6.1 | 5.1 | 6.3 |

As can be deduced from the results shown in Table 3 the GF/Bb treatment attenuated the OVA induced detoriated nesting behavior in a statistically significant way.

TABLE 3

| | Nest score | | | |
|---|---|---|---|---|
| | Control, control diet | Control, GF/Bb diet | OVA mice, control diet | OVA mice, GF/Bb diet |
| Mean | 3.63 | 3.56 | 1.25* | 2.75 |
| s.e. | 0.16 | 0.18 | 0.16 | 0.13 |

Allergen exposed mice demonstrated higher anxiety levels, impaired spatial memory and disturbed nesting behavior, which was prevented and/or treated by consumption of a diet with GF/Bb These deficits were in parallel with decreased expression of brain derived neurotrophic factor (BDNF) messenger RNA (mRNA) and p-glycoprotein in the hippocampi. Importantly, synbiotics normalized OVA-induced aberrant cognitive and molecular changes, as shown in Table 4. The decreased p-glycoprotein mRNA level is indicative of a disrupted blood brain barrier. Foxp3 mRNA level was also decreased by OVA sensitization, but this effect was attenuated by the diet of the present invention. FOxp3 is a transcriptional factor for the regulatory T-cells, which suppress inflammatory response. BDNF plays an important role in normal neural development and is important for the synaptic plasticity and learning and memory. A reduced level of BDNF in mice predicts developmental defects in the brain and sensory nervous system.

In control mice with control diet, the level of p-glycoprotein was set at 1. No significant difference was observed in control mice receiving the GF/Bb diet. In OVA allergic mice receiving the control diet the p-glycoprotein level significantly reduced to about 0.5. In OVA allergic mice receiving the GF/Bb diet this was 0.9 (and not significant different from the healthy control).

In control mice with control diet, the level of BDNF was set at 1. No significant difference was observed in control mice receiving the GF/Bb diet. In OVA allergic mice receiving the control diet this significantly reduced to about 0.45. In OVA allergic mice receiving the GF/Bb diet this was 0.93 (and not significant different from control). No significant difference was observed in control mice receiving the GF/Bb diet.

In control mice with control diet, the level of Foxp3 was set at 1. No significant difference was observed in control mice receiving the GF/Bb diet. In OVA allergic mice receiving the control diet this significantly reduced to about 0.44. In OVA allergic mice receiving the GF/Bb diet this was 1.0 (and not different from control).

In addition, FACS analysis of the homogenized hippocampal cells revealed significant elevation in OVA-induced $CD11c^+F4/80^+CD68^-$macrophages, which were attenuated to control levels by the synbiotic treatment. Synbiotics elevated $CD11b^+CD68F4/80^{low}$ cells.

Allergen exposed mice demonstrated higher anxiety levels and impaired spatial memory. These deficits were in parallel with decreased expression of brain derived neurotrophic factor (BDNF) messenger RNA (mRNA) and p-glycoprotein in the hippocampi. The increased macrophage levels observed in the brains of OVA-allergic mice are likely derived from the circulation, which, in combination with observed decrease in brain blood barrier, implicate periphery-driven monocytes as potential key players in inducing robust decrease in brain function observed in the allergic mice. The present data support the notion that allergy-dependent peripheral inflammation modifies the brain inflammatory status and dampens the cognitive abilities of the animals, suggesting that allergy may play a role in the development and/or progression of neurological disorders and that a diet with GF/Bb may prevent and/or treat this.

Importantly, a diet with GF/Bb normalized all these OVA-induced aberrant cognitive and molecular changes.

Example 3: Dietary Intervention with *B. breve* and Non Digestible Oligosaccharides Improves Cognitive and Behavioural Performance and in Particular Attenuates DSS Induced Gastrointestinal Inflammation and Associated Cognitive and Behavioral Deficits in Mice C57B1/6 mice. as in example 1, were fed a control a control diet, *Bifidobacterium breve* M-16V (2% wt:wt $2 \times 10^9$ CFU/g; probiotic), GF (1% wt:wt, 9:1 scGOS:1cFOS; prebiotic) or a combination of both (GF/Bb) as described. Mice were fed the respective diet 2 weeks before and during induction of colitis for 6 days. Colitis was induced by adding 1.5% dextran sodium sulphate (DSS) to the drinking water. Feces consistency (score 0=normal, 1=soft but with form, 2=diarrhea) and development of blood in the feces (score 0=no blood, 1=positive test, 2=visible fresh blood in feces; colo-rectal test kit, Axon Lab AG, Stuttgart, Germany) and body weight was monitored from the time point DSS was added to the drinking water. In other sets of animal no colitis was induced by DSS.

Animal's behavioral and cognitive changes of the group receiving GF/Bb or the control diet were assessed using a T-maze and an open field paradigms, at day 5 and 6 of the DSS treatment respectively, with the assay described in example 1.

Lymphocytes were collected from Peyer's patches (PP) and mesenteric lymph nodes (MLN) by crushing the tissue on a 100 um cell trainer. Cells isolated from PP, MLN were collected in PBS/2% FCS. Fcγ-receptors were blocked using 10 ug/mL CD16/CD32 antibodies, followed by extracellular staining using CD11c-FITC, CD40-FITC, CD80-APC, CD86-APC, CD103-APC, CD4-FITC and CD69-PerCP-Cy5.5 antibodies (all eBioscience). Cells were fixed using 0.5% paraformaldehyde, or fixed and permeabilized using the using the Foxp3 staining buffer set (eBioscience) according to manufacturer's protocol for intracellular staining. Intracellular staining was performed using Foxp3-APC, ROR-γT-PE, T-bet-PE and GATA3-eFluor660 antibodies (all eBioscience). Flow cytometric analysis was performed using a FACSCantoII and FACSDiVa software (BD Biosciences).

Results

Dietary intervention using GF or GF/Bb improved the fecal consistency score and delayed the onset of the development of blood in the feces. At day 6 in all DSS treated groups the score was above 1.5. Looking at the total AUC of the feces score at day 6, GF, Bb and GF/Bb reduced the blood in faeces score, with the highest effect of the GF/Bb group in which a score of about 2.7 was observed (whereas about 4.2 was observed in the control group, about 3.0 in the Bb group and about 3.7 in the GF group). In the animals without DSS induced colitis, this score was almost 0.

In healthy mice, dietary intervention with *Bifidobacterium breve* M-16V, GF and especially GF/Bb increased the expression of CD80 and CD86 by $CD11c^+$ cells in MLN. DSS treatment enhanced the expression of CD80 and CD86, but suppressed CD40 expression by $CD11c^+$ cells in MLN. In these DSS-treated mice dietary intervention with GF and GF/Bb suppressed CD80 and CD86 expression by MLN $CD11c^+$ cells. In addition, DSS treatment resulted in a lower percentage of CD11c$^+$CD103$^+$ cells in MLN, while dietary intervention *Bifidobacterium breve* M-16V, GF or especially GF/Bb enhanced the frequency of these cells in MLN.

As dietary intervention enhances the relative numbers of CD11c$^+$CD103$^+$ cells in MLN, T cell polarization was affected upon dietary intervention with *Bifidobacterium breve* M-16V, GF or GF/Bb. Therefore, CD4$^+$ T cell phenotype was analyzed by FACS—characterized as activated T cells (CD4$^+$CD69$^+$), T$_h$1 cells (CD4$^+$T-bet$^+$GATA-3$^-$), T$_h$2 cells (CD4$^+$T-bet$^-$GATA-3$^+$), activated T$_h$17 cells (CD4$^+$Ror-γT$^+$Foxp3$^-$) or T$_{reg}$ cells (CD4$^+$Ror-γT$^-$Foxp3$^+$). In MLN, a trend towards increased percentage of activated T cells was observed in DSS treated animals when compared with control mice. Dietary intervention with *Bifidobacterium breve* M-16V, GF or to the largest extend GF/Bb tended to decrease the percentage of activated T cells in MLN. In line with increased percentages of CD11c$^+$CD103$^+$ cells in MLN, in DSS treated mice fed GF/Bb an increase in T$_{reg}$ cells was observed in MLN. A similar trend was observed when mice were fed *Bifidobacterium breve* M-16V or GF (but to a lesser extend). In addition, a trend towards decreased T$_h$17 cells in MLN was observed. Surprisingly, these observations were made in the healthy mice as well.

In short, this indicates that dietary intervention using GF/Bb attenuates the DSS-induced colitis, and inflammation to the highest extent compared to the single components, but that inflammation is present at day 5 and 6 to a high extent in all groups.

Regarding the effects on the cognitive and behavioral performance, it was observed that there was no difference in the locomotor activity between the 4 groups (control diet or GF/Bb, DSS or no DSS treatment) as expressed in total activity (m) in both the T maze and open field test.

In mice receiving the control diet the deleterious effects of DSS intervention on cognitive performance as measured in the T maze model (spatial memory, expressed as mean % of spontaneous alterations) were significant; a decreased from about 78% to about 50%. In the DSS treated mice receiving the diet with GF/Bb these deleterious effects of DSS treatment were not observed, being about 74%, significantly higher than the control DSS group. In the healthy mice receiving GF/Bb a slight increase (about 80%) could be observed.

With regard to behavioral performance (anxiety, expressed as mean time in s spend in center of an open field), in healthy control mice this was about 95 s. In DSS treated mice receiving control diet this was significantly decreased to about 55 s. In the DSS group receiving the GF/Bb diet this decrease was not observed, being about 135 s and significantly higher than in the control DSS group. In the healthy mice receiving a GF/Bb diet a significant increase was observed compared to the healthy control group (about 121 s).

Acute DSS-treatment lead to intestinal inflammation, increased anxiety and impaired spatial memory. All parameters were normalized by synbiotic intervention. The present data support the notion that intestinal inflammation can lead to cognitive and behavioral deficits, but also that synbiotic supplementation may have a therapeutic potential on cognitive and behavioral performance in subjects suffering from intestinal inflammation.

Example 4: Dietary Intervention with *B. breve*, Non-Digestible Oligosaccharides and Glutamine Improves Social Interaction, Cognitive Performance and Behavioural Performance in a Cow's Milk Allergy Model in Mice Pathogen-free, male C3H/HeOuJ mice (4 weeks old, Charles River Laboratories) mice were bred and raised on a cow's milk protein-free diet (Special Diet Services, Witham, UK) and housed on a 12 h light-dark cycle with access to food and water ad libitum. All animal procedures were conducted in accordance with the guidelines of the Dutch Committee of Animal Experiments. The mice were sensitized orally with 0.5 mL homogenized whey protein (40 mg/mL PBS) and cholera toxin (CT, 20 µg/mL PBS, Quadratech Diagnostics) as an adjuvant; sham-sensitized mice received CT alone. Mice were orally boosted once a week for 5 consecutive weeks. One week after the last sensitization, mice were challenged orally with 0.5 mL whey (100 mg/mL PBS).

The mice were fed a control diet, or a combination of *Bifidobacterium breve* M-16V (2% wt:wt 2×10$^9$ CFU/g; probiotic), GF (1% wt:wt, 9:1 scGOS:1cFOS; prebiotic) and glutamine (5 wt %) [GF/Bb/Gln]. Source of GOS; Vivinal-GOS, source of 1cFOS; RaftilinHP. Source of glutamine: Sigma. Diets started 2 weeks before the first sensitization till the end of the experiment.

At the end, the mice were subjected to social interaction and spatial memory tests. Cow's milk allergy is associated with disturbed social interaction and impaired spatial memory, and thus suited to study the effects of dietary intervention there.

Social Interaction Tests

In the morning, the day after oral challenge mice were exposed to a social interaction test. Mice were placed in a 45×45 cm open field, with a small perforated Plexiglas cage located against one wall allowing visual, olfactory and minimal tactile interaction. During the habituation phase, mice were allowed to explore the room for 5 min. During the interaction phase, an age- and gender-matched unfamiliar target mouse was introduced in the cage for an additional 5 min. By using video tracking software (EthoVision 3.1.16, Noldus), an interaction zone around the cage was digitally determined. Time spent in the interaction zone as well as frequency of entering the interaction zone over the selected time period was measured.

T Maze Spatial Memory Performance Test

T Maze Spontaneous Alternation is a behavioral test for measuring exploratory behavior and spatial memory performance in animals, especially rodent models for CNS disorders. This test is based on the willingness of rodents to explore a new environment, i.e. prefer to visit a new arm of the maze rather than a familiar arm. Many parts of the brain—including the hippocampus, septum, basal forebrain, and prefrontal cortex—are involved in this task.

Subjects are first placed in the start arm of the T Maze. Upon leaving the start arm, subjects choose between entering either the left or the right goal arm. With repeated trials, the animals should show less of a tendency to enter a previously visited arm. The percentage of alternation (number of turns in each goal arm) and total trial duration are recorded. This test is used to quantify cognitive deficits in transgenic strains of mice and evaluate novel chemical entities for their effects on cognition. After assessing social interaction on the day after the oral challenge, spontaneous alternation was tested in a T maze set-up. Each mouse was placed in the start arm and was allowed to explore the T maze until one of the goal arms was chosen. The animal was then returned to its home cage and performed a total of 5 trials. The T maze was thoroughly cleaned with 70% ethanol in between trials. The alternation ratio was defined as the amount of trials in which an animal alternated divided by the total amount of trials.

The results in terms of social interaction and T alternation were compared with the results observed for unsensitized mice not subjected to dietary intervention.

Results

The cow's milk allergy model shows a good model for studying social interactions in a variety of ways. In table 4, the time in the interaction zone was significantly reduced for sensitized mice (control-sensitized mice vs. control-unsensitized mice). The effects of reduced social interaction induced by sensitization were diminished for all tested diets but greatly diminished for mice fed GF/Bb. Statistics on the in table 4 mentioned samples were generated using unpaired t-test vs CMA sensitized control to calculate p values. CMA GF/Bb was significantly improved over control CMA mice (p=0.05).

TABLE 4

| | Time spent in interaction zone (sec) | | |
|---|---|---|---|
| | Control, CMA Sensitized mice | CMA GF/Bb | CMA GF/Bb/Gln |
| Mean +/- s.e. | 75 +/- 12.1 (n = 12) | 120 +/- 18.7 (n = 11) | 107 +/- 23.7 (n = 12) |

Surprisingly, also unsensitized mice that were fed the GF/Bb/Gln diet, thus not investigated using the CMA model, showed a statistically demonstrated trend (p<0.10) in seeking longer periods of social interaction as measured by the time spent in the interaction zone over unsensitized mice that were fed the control diet (141+/−23.6 sec vs 199+/−21.7 sec, p=0.08). The effect of the dietary supplementation with GF/Bb/Gln also exceeded that of supplementation with GF/Bb in this unsensitized, non-allergic healthy background.

A second parameter used for measuring social interaction is the frequency of animals entering the interaction zone over a pre-set time interval. Surprisingly, the frequency of animals entering the interaction zone, implying they seek interaction with the age- and gender-matched unfamiliar target mouse, for CMA sensitized mice fed the GF/Bb as well as the GF/Bb/Gln diet was significantly improved (p values for control CMA vs CMA GF/Bb and control CMA vs GF/Bb/Gln as measured are p 0.032 and p 0.0095, resp.). Statistics on the in table 5 mentioned samples were generated using unpaired t-test vs CMA sensitized control to calculate p values.

TABLE 5

| | Frequency of entering the interaction zone | | |
|---|---|---|---|
| | Control, CMA Sensitized mice | CMA GF/Bb | CMA GF/Bb/Gln |
| Mean, +/- s.e. | 8.0 +/- 0.94 (n = 11) | 14.7 +/- 2.76 (n = 11) | 12.7 +/- 1.36 (n = 10) |

The cow's milk allergy model also shows a good model for studying spatial memory using T-maze spontaneous alternation behavioral tests. In table 6, the effects of reduced alternation in the T-maze test induced by sensitization were significantly improved for mice fed a diet with supplementation of GF/Bb (p=0.06) but also supplemented with GF/Bb/Gln (p=0.0005), compared to the situation observed for control CMA-mice. Statistics on the in table 6 mentioned samples were generated using unpaired t-test vs CMA sensitized control to calculate p values.

TABLE 6

| | % Alternation in spatial memory test | | |
|---|---|---|---|
| | Control, CMA Sensitized mice | CMA GF/Bb | CMA GF/Bb/Gln |
| Mean, s.e. | 52.7 +/- 4.3 (n = 9) | 64.6 +/- 3.7 (n = 12) | 81.3 +/- 4.5 (n = 12) |

Surprisingly, the beneficial effects on spatial memory of dietary supplementation with GF/Bb, but also GF/Bb/Gln, versus the control diet without supplementation were also observed in healthy, unsensitized mice. Spatial memory performance of non-allergenic, unchallenged healthy mice fed the GF/Bb supplemented diet showed a 20% increase over the control diet (p 0.03, n=12). For GF/Bb/Gln supplemented mice, this increase showed a clear statistical trend at a 17% increase (p=0.10, n=12).

Example 5: Preterm Formula with B. breve and Non Digestible Oligosaccharides

Preterm formula in powder form comprising per 100 g about 474 kcal, 15.6 g protein, 49.8 g digestible carbohydrates (mainly lactose and maltodextrin), 22.9 g fat and 4.7 g non-digestible oligosaccharides. The protein comprises about 92.5 wt. % casein and whey protein from cow's milk based on total protein in a weight ratio of 1:1.5. About 7.5 wt. % of the protein is free L-glutamine. The non-digestible oligosaccharides are galacto-oligosaccharides (Source Vivinal GOS, Borculo Domo) and fructopolysaccharides (Source RaftilinHP, Orafti) in a weight ratio of 9:1. Due to the EU directives the non digestible disaccharides in the GOS do not qualify as dietary fiber. Hence the fiber content is labeled to be 3.3 g per 100 g powder. $10^7$ cfu of Bifidobacterium breve M-16V (Morinaga) is present per g powder. Fat is for the main part of vegetable origin but also tuna fish oil (source of DHA), algae oil (source of ARA) arachidonic acid (ARASCO, Martek) and egg lipid (source of DHA and ARA) are present as a source of LC-PUFA, resulting in 0.52 wt % ARA based on total fatty acyl chains and 0.40 wt % DHA based on total fatty acyl chains. Furthermore the composition comprises minerals, trace elements, vitamins, and other micronutrients as known in the art and according to guidelines for preterm infants. For a ready to drink formula, the instructions are to dilute 16.9 g powder (3 scoops) with water until a final volume of 100 ml.

Example 6: Nutritional Supplement Enriched in Glutamine

Human milk fortifier in powder form packed in sachets comprising 2.1 g. Based on 100 g powder the composition comprises 25.2 g protein, 52.2 g digestible carbohydrates (mainly maltodextrin), 2 g non digestible oligosaccharides as in example 4, $1.10^9$ cfu B. breve M16-V, the rest being minerals, trace elements and vitamins. The protein comprises of 50 wt % of whey protein hydrolysate and casein hydrolysate in a weight ratio of 1/1 and 50 wt % of free L-glutamine based on total protein. Also 10 g of a fat component rich in ARA and DHA is present.

Example 7: Post Discharge Formula for Use in Premature or Small for Gestational Infants after Discharged from the Hospital Post-discharge formula are marketed for use in premature or small for gestational infants after discharged from the hospital or after when reaching the corrected a terme age, until a corrected age of 6 months. In powder form the formula comprises per 100 g about 491 kcal, 13.4 g protein, 49.1 g digestible carbohydrates (mainly lactose and maltodextrin), 26 g fat and 5.2 g non-digestible oligosaccharides. The protein comprises about 92.5 wt. % casein and whey protein from cow's milk based on total protein in a weight ratio of 1:1.5. About 7.5 wt. % of the protein is free L-glutamine. The non-digestible oligosaccharides are galacto-oligosaccharides (Source Vivinal GOS, Borculo Domo) and fructopolysaccharides (Source RaftilinHP, Orafti) in a weight ratio of 9:1. Due to the EU directives the non digestible disaccharides in the GOS do not qualify as dietary fiber. Hence the fiber content is labeled to be 3.7 g per 100 g powder. $5.10^7$ cfu of *Bifidobacterium breve* M-16V (Morinaga) is present per g powder. Fat is for the main part of vegetable origin but also fish oil, algae oil and egg lipid are present as a source of LC-PUFA are present, resulting in 0.44 wt % ARA based on total fatty acyl chains and 0.33 wt % DHA based on total fatty acyl chains. Furthermore the composition comprises minerals, trace elements, vitamins, L-carnitine, choline, myo-inositol and taurine and nucleotides as known in the art and according to guidelines for preterm infants. For a ready to drink formula, the instructions are to dilute 15.3 g powder (3 scoops) with water until a final volume of 100 ml.

Example 8: Infant Formula for Allergic Infants

In powder form comprising per 100 g about 493 kcal, 11.6 g protein, 52 g digestible carbohydrates (mainly lactose and maltodextrin), 25.6 g fat and 5.9 g non-digestible oligosaccharides. The protein comprises extensively hydrolyzed whey protein and about 5 wt. % of the protein is added free L-glutamine. The non-digestible oligosaccharides are galacto-oligosaccharides (Source Vivinal GOS, Borculo Domo) and fructopolysaccharides (Source RaftilinHP, Orafti) in a weight ratio of 9:1. Due to the EU directives the non digestible disaccharides in the GOS do not qualify as dietary fiber. Hence the fiber content is labeled to be 4.1 g per 100 g powder. $5.10^8$ cfu of *Bifidobacterium breve* M-16V (Morinaga) is present per g powder. Fat is for the main part of vegetable origin but also other lipid sources are present as a source of LC-PUFA, resulting in 0.2 wt % ARA based on total fatty acyl chains and 0.2 wt % DHA based on total fatty acyl chains. Furthermore the composition comprises minerals, trace elements, vitamins, L-carnitine, choline, myo-inositol and taurine and nucleotides as known in the art. For a ready to drink formula, the instructions are to dilute 13.6 g powder (3 scoops) with water until a final volume of 100 ml.

Example 9: Kit for Preterms

A package with 20 sachets with powder comprising glutamine in free amino acid form and non-digestible oligosaccharides. The non-digestible oligosaccharides are galacto-oligosaccharides (Source Vivinal GOS, Borculo Domo) and fructopolysaccharides (Source RaftilinHP, Orafti) in a weight ratio of 9:1. The weight ratio of glutamine to the sum of non-digestible oligosaccharides GOS and FOS is about 1:2. The package also comprises a second set of 20 sachets with $3\times10^9$ cfu of *Bifidobacterium breve* M-16V (Morinaga) per g powder. The package is accompanied with instructios for use of the sachets for preterms, wherein the instructions are expressed in g/100 mL ready-to-feed product (with daily dosage of 150 ml for preterms): 0.2 g/100 mL glutamine and 0.4 g/100 mL GOS/FOS, and 1 g *B. breve*.

The invention claimed is:

1. A method for improving cognitive performance, cognitive development, behavioral performance, behavioral development and/or social interaction in an infant or toddler and/or treating decreased cognitive performance, decreased cognitive development, decreased behavioral performance, decreased behavioral development and/or decreased social interaction in an infant or toddler suffering from a food allergy or from intestinal inflammation, the method comprising administering to the infant or toddler a nutritional composition comprising:
  (a) glutamine in the form of free amino acids, dipeptides and/or tripeptides,
  (b) *Bifidobacterium breve*, and
  (c) at least one non-digestible oligosaccharide selected from the group consisting of fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid-comprising oligosaccharides and uronic acid oligosaccharides.

2. The method according to claim 1, wherein the infant or toddler is a preterm infant, infant small for gestational age (SGA) or infant born via caesarian section.

3. The method according to claim 1, wherein the *Bifidobacterium breve* (*B. breve*) is *B. breve* M-16V.

4. The method according to claim 1, wherein the non-digestible oligosaccharide comprises galacto-oligosaccharides and/or fructo-oligosaccharides.

5. The method according to claim 1, wherein the nutritional composition further comprises protein, fat and/or digestible carbohydrates.

6. The method according to claim 1, wherein the nutritional composition comprises $10^2$ to $10^{13}$ cfu *Bifidobacterium breve* (*B. breve*) per g dry weight of the composition.

7. The method according to claim 1, wherein the nutritional composition comprises 0.5 to 20 wt. % non-digestible oligosaccharides based on dry weight of the nutritional composition.

8. The method according to claim 1, wherein the cognitive performance or cognitive development is memory performance or memory development.

9. The method according to claim 8, wherein the memory performance or memory development involves spatial performance.

10. The method according to claim 1, wherein the nutritional composition further comprises long-chain poly unsaturated fatty acids (LCPUFAs).

11. The method according to claim 10, wherein the LCPUFAs comprise arachidonic acid (ARA) and/or docosahexaenoic acid (DHA).

12. A method for improving cognitive performance, cognitive development, behavioral performance, behavioral development and/or social interaction in an infant or toddler suffering from a food allergy or from intestinal inflammation, the method comprising administering to the infant or toddler a nutritional composition comprising:
  (a) glutamine in the form of free amino acid, dipeptides and/or tripeptides,
  (b) *Bifidobacterium breve*, and
  (c) at least one non-digestible oligosaccharide selected from the group consisting fructo-oligosaccharides, galacto-oligosaccharides, gluco-oligosaccharides, arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid-comprising oligosaccharides and uronic acid oligosaccharides.

13. The method according to claim 1, wherein the infant or toddler suffers from allergy.

14. The method according to claim 1, wherein the infant or toddler suffers from intestinal inflammation.

* * * * *